(12) United States Patent
Deen

(10) Patent No.: US 12,150,630 B2
(45) Date of Patent: Nov. 26, 2024

(54) WIRE GRIPPING DEVICE

(71) Applicant: Covidien LP, Mansfield, MA (US)

(72) Inventor: Daniel Deen, Long Beach, CA (US)

(73) Assignee: Covidien LP, Mansfield, MA (US)

( * ) Notice: Subject to any disclaimer, the term of this patent is extended or adjusted under 35 U.S.C. 154(b) by 935 days.

(21) Appl. No.: 17/143,026

(22) Filed: Jan. 6, 2021

(65) Prior Publication Data

US 2022/0211359 A1    Jul. 7, 2022

(51) Int. Cl.
*A61B 17/00* (2006.01)
*A61M 25/09* (2006.01)

(52) U.S. Cl.
CPC .............. *A61B 17/00* (2013.01); *A61M 25/09* (2013.01); *A61B 2017/00367* (2013.01); *A61B 2017/00486* (2013.01)

(58) Field of Classification Search
CPC .......... A61B 17/00; A61B 2017/00367; A61B 2017/00486; A61M 25/09; A61M 25/0113; A61M 2025/09116; A61M 25/09041
See application file for complete search history.

(56) References Cited

U.S. PATENT DOCUMENTS

| | | | |
|---|---|---|---|
| 5,312,338 A * | 5/1994 | Nelson ............ | A61M 25/09041 604/528 |
| 5,392,778 A * | 2/1995 | Horzewski ...... | A61M 25/09041 600/434 |
| 5,524,635 A * | 6/1996 | Uflacker .......... | A61B 17/22012 600/585 |
| 5,902,306 A * | 5/1999 | Norman ............ | A61B 17/1697 606/104 |
| 6,533,772 B1 | 3/2003 | Sherts et al. | |
| 7,972,282 B2 | 7/2011 | Clark et al. | |
| 9,295,815 B2 * | 3/2016 | Stevens ........... | A61M 25/09041 |
| 9,375,553 B2 | 6/2016 | Chrisman | |
| 10,478,599 B2 | 11/2019 | Chrisman | |
| 2004/0034311 A1 * | 2/2004 | Mihalcik ............ | A61B 1/00195 600/585 |

(Continued)

FOREIGN PATENT DOCUMENTS

WO    2019081962    5/2019

OTHER PUBLICATIONS

Extended Search Report from counterpart European Application No. 21214721.9 dated May 20, 2022, 8 pp.

*Primary Examiner* — David Hamaoui
*Assistant Examiner* — Rumaisa Rashid Baig
(74) *Attorney, Agent, or Firm* — Shumaker & Sieffert, P.A.

(57) ABSTRACT

A gripping device is configured to grip a medical device wire or shaft and includes a collet defining a collet lumen, a collet sleeve including a flange and configured to house the collet and defining a collet sleeve lumen, and a cam configured to house the collet sleeve and defining a cam lumen, each of the collet, collet sleeve, and cam lumens configured to receive a medical device wire or shaft. The device includes a housing including a proximal portion configured to house the collet, collet sleeve and a distal portion. The cam is rotatably attached to the distal portion and is configured to move the collet sleeve and collet towards the proximal portion upon rotation of the cam from a release position to a grip position and to move towards the distal portion of the housing upon rotation of the cam from the grip position to the release position.

23 Claims, 8 Drawing Sheets

(56) References Cited

U.S. PATENT DOCUMENTS

| | | | |
|---|---|---|---|
| 2004/0215108 A1* | 10/2004 | Windheuser | A61M 25/09041 604/528 |
| 2005/0096566 A1 | 5/2005 | Arnott | |
| 2009/0124934 A1* | 5/2009 | Rabbitte | A61M 25/09041 600/585 |
| 2010/0211006 A1* | 8/2010 | Schmidt-Sorensen | A61M 25/09041 604/95.01 |
| 2013/0103001 A1 | 4/2013 | BenMaamer et al. | |
| 2014/0171919 A1* | 6/2014 | Blacker | A61B 34/30 604/533 |
| 2014/0324026 A1* | 10/2014 | Chrisman | A61M 25/09041 604/528 |
| 2015/0105650 A1* | 4/2015 | Burkett | A61B 1/3137 74/543 |
| 2019/0133569 A1* | 5/2019 | Malkowski | A61B 17/0482 |
| 2020/0060693 A1* | 2/2020 | Sweitzer | A61B 17/1613 |
| 2020/0398031 A1* | 12/2020 | Gill | A61M 25/09041 |

\* cited by examiner

WIRE GRIPPING DEVICE

TECHNICAL FIELD

The disclosure relates to medical devices.

BACKGROUND

Some medical devices include a wire, such as a guidewire or a push wire. During a medical procedure, a clinician may control movement of the wire, such as by applying a distal pushing force and/or a torqueing motion to a proximal portion of the wire to navigate a distal portion. The wire may be relatively thin and can also include a hydrophilic coating, both of which may make it difficult for a clinician to manually grip, e.g., between fingers. A wire gripper, also referred to as a wire torquer in some cases, may attached to the wire to enable a clinician to better control the wire, e.g., to apply an adequate pushing, pulling, and/or twisting/torqueing force to the wire.

SUMMARY

The present disclosure describes a wire gripping device including a locking cam configured to be operable by one hand of a user, such as a clinician, to alternately grip and/or release a wire, or other elongate shaft such as a tube or hypotube, of a medical device. The wire gripping device includes a one handed locking cam and a collet. The wire gripping device may be small, light, and enable one handed operation of the wire gripping device, e.g., pushing, pulling, torqueing, and repositioning and regripping of the wire. For example, the wire gripping device may enable a user to push a cam of the wire gripping device to cause the wire gripping device to grip the wire, push, pull, and or torque the wire using the wire gripping device, and push the cam to release the wire, reposition the wire gripping device on the wire and push a cam to regrip the wire for subsequent pushing, pulling, and/or torqueing, all with one hand.

Clause 1: In some examples, a device includes a collet defining a collet lumen, the collet lumen configured to receive a medical device wire or shaft; a collet sleeve configured to at least partially house the collet, wherein the collet sleeve defines a collet sleeve lumen configured to receive the medical device wire or shaft, wherein the collet sleeve comprises a flange; and a cam configured to at least partially house the collet sleeve, wherein the cam defines a cam lumen configured to receive the medical device wire or shaft; and a housing includes a proximal portion configured to at least partially house the collet and collet sleeve; and a distal portion, wherein the cam is rotatably attached to the distal portion, wherein the cam is configured to move the collet sleeve and collet towards the proximal portion of the housing upon rotation of the cam relative to the housing from a release position to a grip position, wherein the cam is configured to enable the collet sleeve and collet to move towards the distal portion of the housing upon rotation of the cam relative to the housing from the grip position to the release position.

Clause 2: In some examples of the device of clause 1, the medical device wire or shaft comprises a guidewire, a guide extension catheter wire, a wire coupled to an implant, or a tube or hypotube.

Clause 3: In some examples of the device of any of clauses 1 or 2, a proximal end of the collet defines one or more slots, wherein the one or more slots are configured to compress radially inwards in response to rotation of the cam relative to the housing from the release position to the grip position.

Clause 4: In some examples of the device of any of any of clauses 1-3, the collet comprises one or more tabs extending radially outwards at a proximal end of the collet, wherein a proximal surface of each tab tapers towards the proximal end of the collet.

Clause 5: In some examples of the device of any of clauses 1-4, an inner surface of the proximal portion of the housing is tapers towards the proximal end of the housing and is configured to engage the proximal surfaces of the one or more tabs.

Clause 6: In some examples of the device of clause 5, the collet sleeve is configured to move the collet towards the proximal portion of the housing upon being pushed by the cam, thereby forcing the proximal surfaces of the one or more tabs to engage the inner surface of the proximal portion of the housing, wherein the inner surface of the proximal portion of the housing is configured to resist movement of the collet and cause the one or more tabs to apply a radially inward force to compress the collet.

Clause 7: In some examples of the device of any of clauses 5 or 6, the collet is biased radially outwards to enable the proximal surfaces of the one or more tabs to engage the inner surface of the proximal portion of housing and move the collet and collet sleeve in a distal direction relative to the housing upon rotation of the cam from the grip position to the release position.

Clause 8: In some examples of the device of clause 7, upon rotation of the cam from the grip position to the release position, a diameter of the collet lumen is configured to increase and thereby decrease a grip force on the device.

Clause 9: In some examples of the device of any of clauses 1-8, rotation of the cam from the release position to the grip position is configured to push compress the collet, and wherein the collet is configured to decrease a diameter of the collet lumen and increase a grip force on the medical device wire or shaft upon compression of the collet.

Clause 10: In some examples of the device of any of clauses 1-9, the cam comprises one or more posts, the one or more posts configured to be rotatably attached within one or more apertures of the housing, wherein the cam is configured to push the housing in a distal direction via the one or more posts while pushing the collet sleeve in a proximal direction via the flange.

Clause 11: In some examples of the device of any of clauses 1-10, the cam is configured to apply a radial force compressing the collet, via the one or more tabs, in response to rotation of the cam relative to the housing.

Clause 12: In some examples of the device of any of clauses 1-11, the cam is configured to remain in the grip position until a force greater than a predetermined threshold force is applied to the cam in a release direction.

Clause 13: In some examples, a method includes introducing a medical device wire or shaft into a device lumen of a device, wherein the device comprises: a collet defining a collet lumen; a collet sleeve configured to at least partially house the collet, wherein the collet sleeve defines a collet sleeve lumen, wherein the collet sleeve comprises a flange; and a cam configured to at least partially house the collet sleeve, wherein the cam defines a cam lumen; and a housing includes a proximal portion configured to at least partially house the collet and collet sleeve; and a distal portion, wherein the cam is rotatably attached to the distal portion, wherein the device lumen is at least partially defined by the collet lumen, the collet sleeve lumen, and the cam lumen;

rotating the cam relative to the housing from release position towards a grip position, wherein the cam is configured to move the collet sleeve and collet towards the proximal portion of the housing upon rotation of the cam relative to the housing from the release position to the grip position, and wherein the cam is configured to enable the collet sleeve and collet to move towards the distal portion of the housing upon rotation of the cam relative to the housing from the grip position to the release position.

Clause 14: In some examples of the method of clause 13, the medical device wire or shaft comprises a guidewire, a guide extension catheter wire, a wire coupled to an implant, or a tube or hypotube.

Clause 15: In some examples of the method of any of clauses 13 or 14, a proximal end of the collet defines one or more slots, wherein rotating the cam from the release position towards the grip position comprises compressing the one or more slots radially inwards.

Clause 16: In some examples of the method of any of clauses 13-15, the method further includes rotating the cam from the grip position towards the release position; and repositioning the device along the medical device wire or shaft.

Clause 17: In some examples of the method of any of clauses 13-16, the method further includes locking the cam in a grip position until a force greater than a predetermined threshold force is applied to the cam in a release direction.

Clause 18: In some examples, a medical device includes a collet defining a collet lumen, the collet lumen configured to receive a medical device wire or shaft; a collet sleeve configured to at least partially house the collet, wherein the collet sleeve defines a sleeve lumen configured to receive the medical device wire or shaft, wherein the collet sleeve comprises a flange; and a cam configured to at least partially house the collet sleeve, wherein the cam defines a cam lumen configured to receive the medical device wire or shaft; and a housing includes a proximal portion configured to at least partially house the collet and collet sleeve; and a distal portion, wherein the cam is rotatably attached to the distal portion, wherein the cam is configured to increase a push force against the flange upon rotation of the cam relative to the housing from a release position to a grip position and thereby move the collet sleeve and collet towards the proximal portion of the housing, wherein the cam is configured to move the collet sleeve and collet towards the proximal portion of the housing upon rotation of the cam relative to the housing from a release position to a grip position, wherein the cam is configured to enable the collet sleeve and collet to move towards the distal portion of the housing upon rotation of the cam relative to the housing from the grip position to the release position, wherein rotation of the cam from the release position to the grip position is configured to push compress the collet, and wherein the collet is configured to decrease a diameter of the collet lumen and increase a grip force on the medical device wire or shaft upon compression of the collet.

Clause 19: In some examples of the medical device of clause 18, upon rotation of the cam from the grip position to the release position, the diameter of the collet lumen is configured to increase to decrease the grip force on the medical device.

Clause 20: In some examples of the medical device of any of clauses 18 or 19, the cam is configured to remain in the grip position until a force greater than a predetermined threshold force is applied to the cam in a release direction.

The details of one or more examples are set forth in the accompanying drawings and the description below. Other features, objects, and advantages will be apparent from the description and drawings, and from the claims.

DETAILED DESCRIPTION

Figure 1:
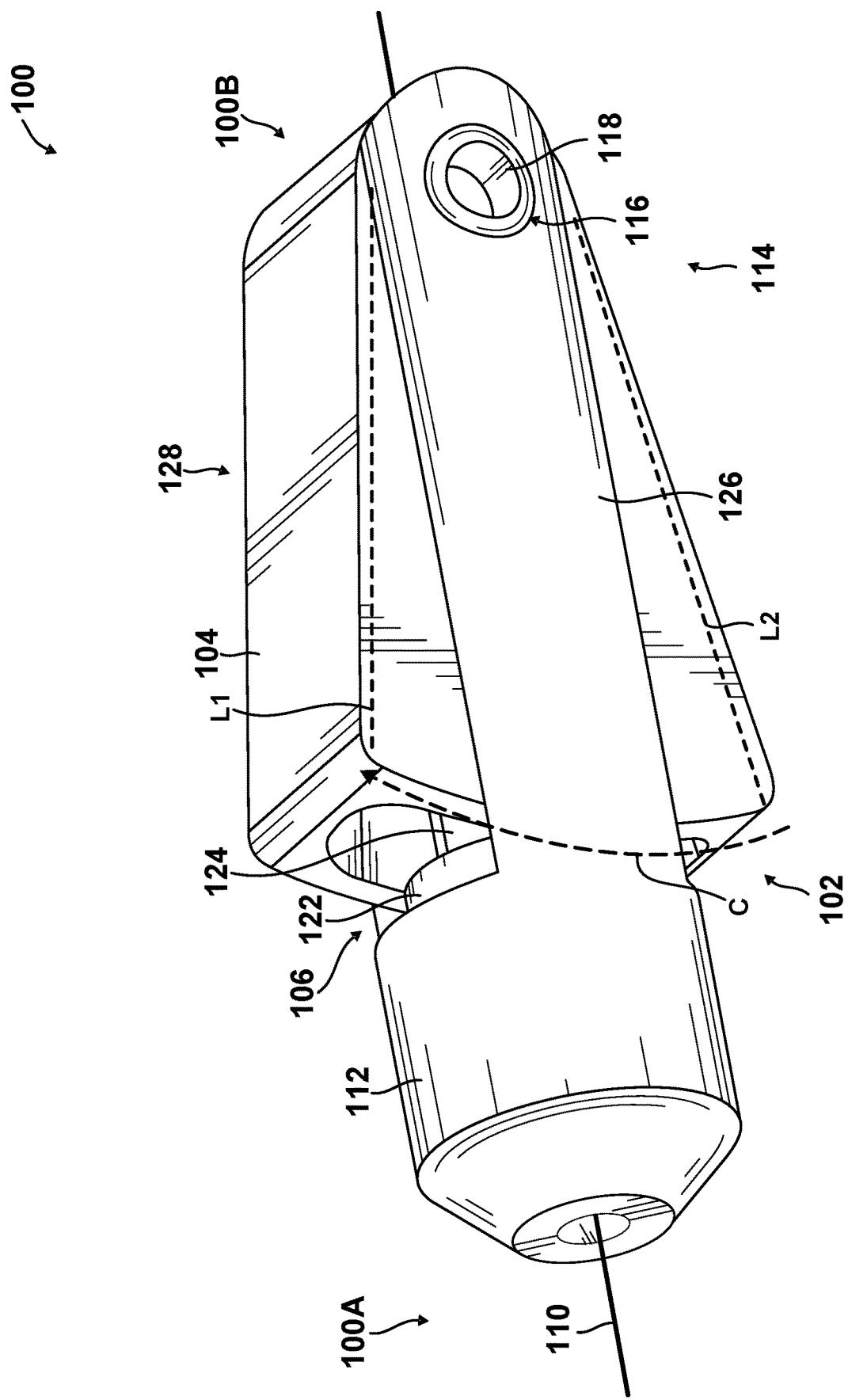
FIG. 1 is a perspective view illustrating an example wire gripping device.

The present disclosure describes wire gripping devices including a locking cam operable by one hand of a user to alternately grip and/or release a wire, or other elongate shaft such as a tube or hypotube, of a medical device. The wire can be, for example, a guidewire, a push wire of a guide extension catheter, a wire coupled to an implant or embolization device (e.g., a coil) or another elongated medical device (e.g. those used in intravascular procedures) that may be gripped and manipulated by a clinician during a medical procedure.

The gripping device defines a device lumen configured to receive the medical device wire, e.g., and enable the medical device wire to extend through the entire gripping device from a proximal end to a distal end of the gripping device. The device lumen can be defined by one or more structures of the gripping device, including a collet, a housing, and a collet sleeve.

In some examples, the gripping device includes a collet defining a lumen configured to receive the medical device wire, a collet sleeve configured to at least partially house the collet, the collet sleeve defining a collet sleeve lumen configured to receive the medical device wire, and a cam configured to at least partially house the collet sleeve and defining a cam lumen configured to receive the medical device wire. The gripping device may also include a housing that includes a proximal portion configured to at least partially house the collet and collet sleeve and a distal portion to which the cam is rotatably attached.

The cam is configured to be rotated relative to the housing from a grip position to a release position and vice versa. In the grip position of the cam, the medical device wire or shaft is secured within the device lumen, e.g., to enable the gripping device and the medical device wire to move as one unit. That is, when the cam is in the grip position, as the gripping device is moved (e.g., pushed or pulled along a longitudinal axis of the medical device wire and/or torqued about the longitudinal axis), the medical device wire moves with the gripping device. In this way, the gripping device provides structure for a user to grip and may facilitate controllable application of axial force, e.g., push and pull along a longitudinal axis of the medical device wire, and torqueing of the medical device wire, e.g., rotation about the longitudinal axis of the medical device wire. For example, a medical device wire or shaft may be relatively thin and/or may include a lubricious coating (e.g., a hydrophilic coating) that may make direct gripping and manipulation of the medical device wire itself by hand relatively difficult. The gripping device may be configured to secure relative to the medical device wire to enable a user to manipulate the guidewire by manipulating of the gripping device. The gripping device may be sized for a user to more comfortably manipulate the medical device wire in comparison to directly gripping the medical device wire.

In some examples, the gripping device may enable a user to grip and/or lock the gripping device on the medical device wire, manipulate the medical device wire via the gripping device, and release and reposition the gripping device with one hand. In the release position, the gripping device is configured to move relative to the gripping wire. This can enable a clinician to reposition the gripping device relative to the medical device wire (e.g., to move the gripping device proximally or distally along a longitudinal axis of the medical device wire and/or to change a rotational position of the gripping device relative to the medical device wire) or introduce or remove medical device wire from the device lumen of the gripping device.

The cam of the gripping device may be configured to push a flange of the collet sleeve to move the collet sleeve and collet in the proximal direction relative to the cam and the housing when the cam is rotated in the direction of the grip position, e.g., from a release position towards the grip position. The collet may include one or slots that enable the diameter of the collet to be decreased when a radial force is applied via one or more tabs at the distal end of the collet. In some examples, the one or more tabs may be tapered towards the proximal end of the collet and may be configured to engage with inner surfaces of the proximal portion of the housing, e.g., to resist movement of the collet towards in the proximal direction and convert the movement and/or push force from the cam in the proximal direction to movement and/or a force in the radial direction via the tabs to compress the collet lumen and increase a grip force on the medical device wire. In some examples, the collet is configured to be biased radially outwards, e.g., at least partially elastic, and exert an elastic and/or spring force to resist the radial force, such that when the cam is rotated in the direction of the release position, e.g., from the grip position towards the release position, the collet may decompress. Such decompression of the collet decreases the grip force of the collet on the medical device wire or shaft and causes radially outward movement and/or a radially outward directed force on the tabs, which may engage with the inner surfaces of the housing and convert the radially outward movement and/or force to movement and/or a force in the distal direction.

In some examples, the wire gripping device may be configured to lock in the grip position and/or in the release position. For example, the cam may be configured to lock or remain in a grip position until a force greater than a predetermined threshold force is applied to the cam in the release direction.

The wire gripping device may be small, light, and enable one handed operation of the wire gripping device by a clinician, e.g., pushing, pulling, torqueing, and repositioning and regripping of the wire. For example, the wire gripping device may enable a user to push a cam of the wire gripping device to cause the wire gripping device to grip the wire, push, pull, and or torque the wire using the wire gripping device, and push the cam to release the wire, reposition the wire gripping device on the wire, and push a cam to regrip the wire for subsequent pushing, pulling, and/or torqueing, all with one hand.

FIG. 1 is a conceptual perspective view illustrating an example wire or shaft gripping device 100. In the example shown, wire gripping device 100 includes housing 102, cam 104, collet sleeve 106, and collet 108 (not visible in FIG. 1). Cam 104 is illustrated in a cam position between a release position and a grip position, e.g., between fully releasing and fully gripping medical device wire 110 received within and extending through a device lumen of wire gripping device 100 in the example shown. In some examples, medical device wire 110 is a guidewire. In other examples, medical device wire 110 is a guide extension catheter wire (e.g., a push wire) or a wire connected to an embolization device. In still other examples, medical device wire 110 is any other suitable elongated element or shaft, such as a tube, hypotube, or catheter body, that is part of a medical device or used to facilitate a medical procedure. The elongated element can be, for example, configured to be introduced into a hollow anatomical structure of a patient (e.g., a blood vessel).

In the example shown in FIG. 1, housing 102 includes a proximal portion 112 configured to house collet sleeve 106. Housing 102 has any suitable shape. In some examples, proximal portion 112 is substantially cylindrical (e.g., a majority of the proximal portion defines a cylinder-like shape) and has a substantially circular (e.g., circular or nearly circular to the extent permitted by manufacturing tolerances) cross-sectional shape, the cross-section being take in a direction orthogonal to a longitudinal axis of wire gripping device 100, which runs parallel to medical device wire 110 shown in FIG. 1. Other cross-sectional shapes can also be used.

Housing 102 also includes a distal portion 114 at a distal end 100B of wire gripping device 100. Distal portion 114 is configured to rotatably connect to cam 104. Distal portion 114 can be integrally formed with and/or separate from and mechanically attached to proximal portion 112. In the example shown, distal portion 114 comprises two arms 126, 128 each including an aperture 116 configured to receive a post 118 of cam 104 and separated from each other and configured to accept cam 104. Proximal portion 112 at a proximal end 100A of wire gripping device 100 may be configured to at least partially house a collet 108 and a collet sleeve 106. Housing 102 may be made of metal, plastic, or any suitable material for providing structure for wire gripping device 100.

Cam 104 includes slot 140 configured to receive collet sleeve 106. Cam 104 may include posts 118 configured to fit within apertures 116 and enable cam 104 to rotate relative to housing 102. Cam 104 may be made of metal, plastic, or any suitable material for providing structure to push against both housing 102 and collet sleeve 106.

Collet sleeve 106 is configured to receive and house collet 108 and may be configured to be received by cam 104. In the example shown in FIG. 1, collet sleeve 106 includes flange 122 configured to contact cam 104 and provide structure for cam 104 to push against and thereby move collet sleeve 106 relative to housing 102. Flange 122 may be integrally formed with and/or separate from and mechanically attached to collet sleeve body 124. Collet sleeve 106 has any suitable shape. In some examples, collet sleeve 106 is substantially cylindrical having a substantially circular cross-sectional shape, the cross-section being take in a direction orthogonal to the longitudinal axis of wire gripping device 100. Collet sleeve 106 may be made of metal, plastic, or any suitable material for providing structure for cam 104 to push against to move collet sleeve 106 relative to housing 102.

In the example shown, cam 104 has a length that varies relative to the longitudinal axis of wire gripping device 100 in a circumferential direction C, depending on a position of cam 104 relative to housing 102. In particular, cam 104 has a length L1 at a first circumferential position, e.g., the release position, and its length increases in the circumferential direction to a length L2 at a second circumferential position, e.g., the grip position. The circumferential direction C can, but need not, extend along an outer perimeter of an imaginary circle. Rather, the circumferential direction C can extend along any curve. Lengths L1 and L2 can be measured, for example, through a center of cam 104 from end to end of cam 104, along an edge of cam 204 from end to end of cam 104, or the like, and in a manner consistent with each other.

In some examples, cam 104 is configured to move the collet sleeve and/or increase a push force against flange 122 in the proximal direction, e.g., in the axial direction from distal end 100B to proximal end 100A. For example, a user may rotate cam 104 in a grip direction relative to housing 102, e.g., the grip direction being the direction of rotation of cam 104 from a greater cam 104 length L2 to lesser cam 104 length L1 and the same as circumferential direction C in the example shown. When cam 104 is rotated relative to housing 102 in the grip direction, the length of the portion of cam 104 contacting flange 122 and apertures 116 of housing 102 increases and causes the push force against flange 122. For example, cam 104 is mechanically connected to housing 102 via posts 118, which are rotatably supported within apertures 116, and when cam 104 is rotated from a release position with a length L1 to a grip position with a length L2 that is greater than L1, cam 104 pushes housing 102 in a distal direction, e.g., in the axial direction from proximal end 100A to distal end 100B, via posts 118. At the same time, cam 104 pushes collet sleeve 106 in the proximal direction via flange 122. In other words, rotating cam 104 in the grip direction increases the length of the mechanical structure contacting flange 122 and apertures 116, namely, cam 104. Similarly, when cam 104 is rotated in the opposite direction the length of cam 104 in contact between flange 122 and apertures 116 decreases, decreasing the push force in the proximal direction on collet sleeve 106 and the push force in the distal direction on housing 102.

In some examples, cam 104 increases the push force against flange 122 when rotated in the grip direction and causes collet sleeve 106 to move towards the proximal end of housing 102 within housing 102. Collet 108 may be at least partially housed within collet sleeve 106, and collet sleeve 106 may be configured to push collet 108 upon being pushed by cam 104. In some examples, collet 108 may include a lumen configured to receive medical device wire 110.

In some examples, and as illustrated and described below with reference to FIG. 2, when cam 104 is rotated in the grip direction, cam 104 is configured to apply a push force in the proximal axial direction (along the longitudinal axis of wire gripping device 100) to collet 108 and one or more inner surfaces of housing 102. Collet 108 and the one or more inner surfaces of housing 102 are configured to convert this push force in the proximal axial direction to a radially inwards force, which may compress collet 108 (e.g., converting the movement of collet 108 in the proximal axial direction to a radially inwards movement). The compression of collet 108 causes a lumen of collet 108 to contact and grip medical device wire or shaft 110, e.g., collet 108 may increase a grip force on medical device wire 110 when cam 104 is rotated from the release position to the grip position.

In some examples, collet 108 may be configured is biased radially outwards, e.g., collet 108 may be at least partially elastic such that collet 108 may push radially outwards in resistance to a radially inwards force. In some examples, when cam 104 is rotated in the opposite direction, e.g., in the release direction or from the grip position towards the release position, collet 108 decompresses via a radially outwards elastic force and/or spring force and may cause movement in the radially outwards direction. Collet 108 and the one or more inner surfaces of housing 102 may then convert the spring force and/or radially outwards movement to a push force in the distal axial direction on collet 108 and/or movement of collet 108 in the distal axial direction. In other words, rotating cam 104 in the release direction may decrease the push force on collet 108 which may decrease a grip force on medical device wire 110.

Figure 2:
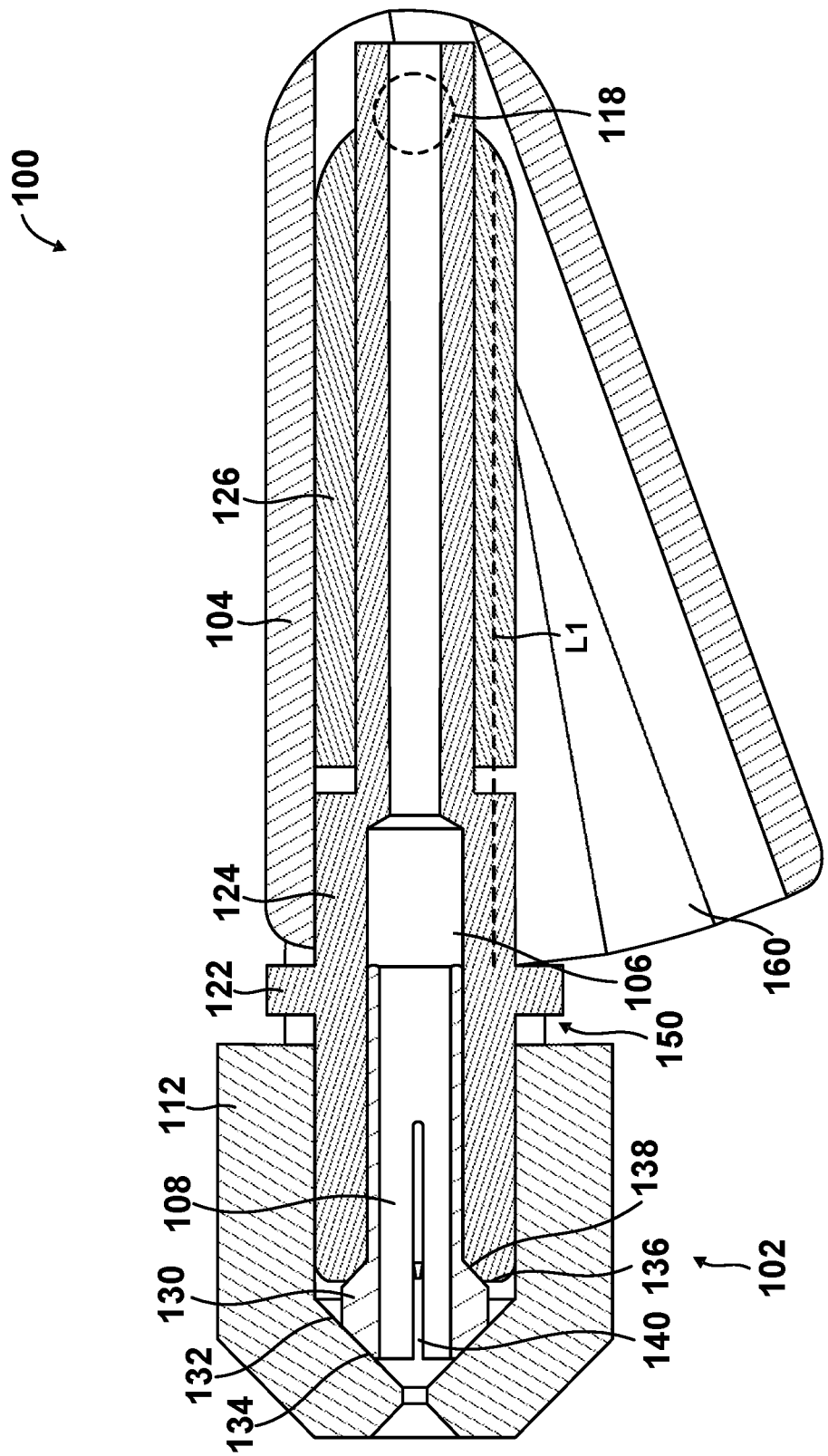
FIG. 2 is cross-sectional view of an example wire gripping device with a cam in a release position.

FIG. 2 is a conceptual cross-sectional view of an example wire gripping device 100 with a cam in a release position, the cross-section being taken in a direction parallel to the longitudinal axis of wire gripping device 100 and through a longitudinal center of gripping device 100. Housing 102, cam 104, collet sleeve 106, and collet 108 of wire gripping device 100 are shown in FIG. 2.

In the example shown, cam 104 is illustrated in the release position in which cam 104 is rotated such that the length of cam 104 between posts 118 and flange 122 is L1. In the example shown, cam 104 includes a tapered and or shaped inner surface 160 which may be configured to mate with collet sleeve 106 and thereby lock cam 104 in a grip position and is visible in FIG. 2 by virtue of cam 104 being in the release position. For example, inner surface 160 may be configured to cause cam 104 to remain in the grip position, e.g., illustrated in FIG. 3 below, until a force greater than a predetermined threshold force is applied to the cam in the release direction. In other examples, inner surface 160 of cam 104 may or may not be shaped in this manner, and cam 104 may be configured to remain in the grip position until a force greater than a predetermined threshold force is applied to the cam in the release direction.

In some examples, the grip position may correspond to the circumferential position, i.e., rotational position, at which the length of cam 104 between posts 118 and flange 122 is a maximum, e.g., L2. In other examples, the grip position may correspond to a different circumferential and/or rotational position of cam 104. For example, the outer circumferential surface of cam 104 that engages with and/or contacts flange 122 may be flattened such the length L2 is at a circumferential position before cam 104 is rotated all the way to the grip position. In other words, the circumferential and/or rotational position of cam 104 corresponding to length L2 may be between the grip position and the release position, and may be substantially near the grip position, and the length of cam 104 between posts 118 and flange 122 at the circumferential and/or rotational position corresponding to the grip position may be less than L2. As a clinician and/or user rotates cam 104 in the grip direction past the circumferential and/or rotational position corresponding to L2 to the grip position, the length of cam 104 between posts 118 and flange 122 may decrease and the elastic force of collet 108, as further described below, may cause collet sleeve 106 to move and/or exert a force in the distal direction on cam 104 thereby locking cam 104 in the grip rotational position. For example, the elastic force of collet 108 may cause flange 122 to push against cam 104 in the distal direction such that cam 104 is prevented from rotating in the release direction until a clinician (or other user) applies a force greater than a predetermined threshold force to cam 104 in the release direction, e.g., the release direction being the rotational direction opposite circumferential direction C as illustrated in FIG. 1.

Figure 3:
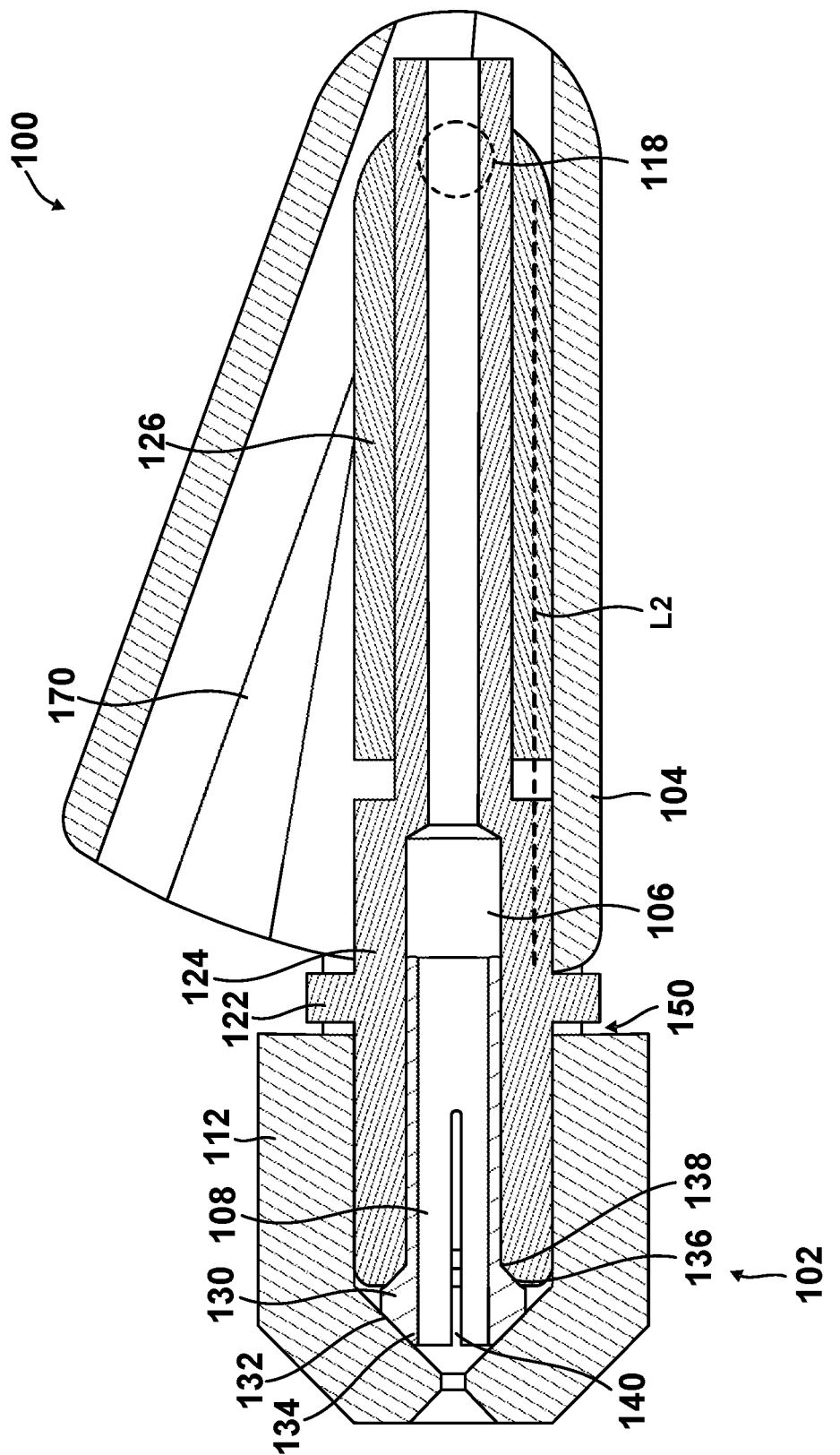
FIG. 3 is a cross-sectional view of an example wire gripping device with a cam in a grip position.

In some examples, any suitable means for locking cam 104 to remain in the grip position until a force greater than a predetermined threshold force is applied to the cam in the release direction may be used. Similarly, cam 104 may be configured to lock in the release position, e.g., either by a shaped inner surface 170 as illustrated in FIG. 3, a flattened outer circumferential surface portion, or any other suitable means.

In the example shown, collet 108 is partially housed within collet sleeve 106. Collet 108 defines one or more slots 140 at one or more positions around a perimeter of collet 108 (referred to herein as circumferential positions although collet 108 may not be circular in cross-section in all examples) and having a length that is less than the entire length of collet 108, e.g., 10% to 75%, such as 10%, 25%, 50%, or 75% the length of collet 108 in the axial direction. In some examples, each slot 140 may have a width sufficient to allow collet 108 to decompress and contact and grip medical device wire 110.

As shown, collet 108 may include one or more tabs 130. Tabs 130 may extend radially outwards from another part of collet 108 and in some examples, are located at a proximal portion (e.g., at a proximal end) of collet 108. In some examples, tabs 130 may include proximal surfaces 134 that taper towards the proximal end of collet 108, and tabs 130 may include distal surfaces 136 that taper towards the distal end of collet 108.

In the example shown, housing 102 may include one or more inner surfaces 132 that taper towards the proximal end of housing 102. In the example shown, collet sleeve 106 may include one or more collet sleeve proximal surfaces 138 that taper away from the proximal end of collet sleeve 106.

In some examples, collet sleeve proximal surfaces 138 are configured to engage with distal surfaces 136, e.g., to push tabs 130 and collet 108 in a proximal axial direction. Inner surfaces 132 may be configured to engage with proximal surfaces 134 of tabs 130, and to cause and/or convert proximal axial movement and/or at least a portion of proximal axial force into a radially inwards movement and/or force, respectively. For example, when tabs 130 are pushed by collet sleeve 106 via surfaces 138/136, proximal surfaces 134 contact inner surfaces 132 which allow collet 108 to move in the proximal axial direction via proximal surfaces 134 sliding along inner surfaces 132 while forcing tabs 130 radially inwards and thereby exerting a radially inwards force on tabs 130 to compress collet 108. Slots 140 are configured to allow collet 108 to compress and reduce a diameter of the collet lumen in response to the radially inwards force and/or movement of tabs 130 and increase a grip force on medical device wire 110 disposed with the collet lumen (not shown in FIG. 2).

In the example shown, wire or shaft gripping device 100 includes spacer 146, which may be configured to constrain collet sleeve 106 to movement substantially in the axial direction.

In operation, when cam 104 is rotated in the grip direction, cam 104 may push against apertures 116 (not shown in FIG. 2) in the distal axial direction and against flange 122 in the proximal axial direction thereby decreasing space 150 between flange 122 and proximal portion 112 of housing 102 and moving and/or increasing the push force on collet sleeve 106 in the proximal axial direction relative to housing 102.

Collet sleeve 106 may then move and/or increase a push force on collet 108 in the proximal axial direction via engagement and/or contact of collet sleeve proximal surfaces 138 with distal surfaces 136 of tabs 130. Tabs 130 may then move and/or increase a push force in the proximal axial direction and proximal surfaces 134 may engage with and/or contact inner surfaces 132 to simultaneously move tabs 130 in the proximal axial direction and the radially inwards direction, and/or proximal surfaces 134 may engage with and/or contact inner surfaces 132 to convert at least a portion of the push force on tabs 130 in the proximal axial direction to a force in the radially inwards direction. In response to the radially inwards force and/or movement of tabs 130, collet 108 may compress the collet lumen and/or increase the grip force on medical device wire 110 disposed within the collet lumen.

Similarly, in operation when cam 104 is rotated in the release direction, cam 104 may decrease the push force against apertures 116 (not shown in FIG. 2) in the distal axial direction and against flange 122 in the proximal axial direction, thereby allowing collet sleeve 106 to move in the distal axial direction and/or decrease the push force on tabs 130 in the proximal axial direction. Collet 108 may elastically push back against the radially inwards movement and/or force of tabs 130, and may cause the collet lumen to decrease the grip force on medical device wire 110 and/or decompress (e.g., expand) and move tabs 130 and collet 108 in the distal axial direction via the engagement of inner surfaces 132 and proximal surfaces 134.

FIG. 3 is a cross-sectional view of an example wire gripping device 100 with a cam in a grip position in which cam 104 is rotated such that the length of cam 104 between posts 118 and flange 122 is L2. As shown in FIG. 3, cam 104 includes a tapered and or shaped inner surface 170 which may be configured to mate with collet sleeve 106 and thereby lock cam 104 in the release position and is visible in FIG. 3 by virtue of cam 104 being in the grip position.

In operation, when cam 104 is rotated in the release direction, cam 104 may decrease the push force against apertures 116 (not shown in FIG. 3) in the distal axial direction and against flange 122 in the proximal axial direction, thereby allowing collet sleeve 106 to move in the distal axial direction and/or decrease the push force on tabs 130 in the proximal axial direction. Collet 108 may elastically push back against the radially inwards movement and/or force of tabs 130, and may cause the collet lumen to decrease the grip force on medical device wire 110 and/or decompress (e.g., expand) and move tabs 130 and collet 108 in the distal axial direction via the engagement of inner surfaces 132 and proximal surfaces 134.

Figure 4:
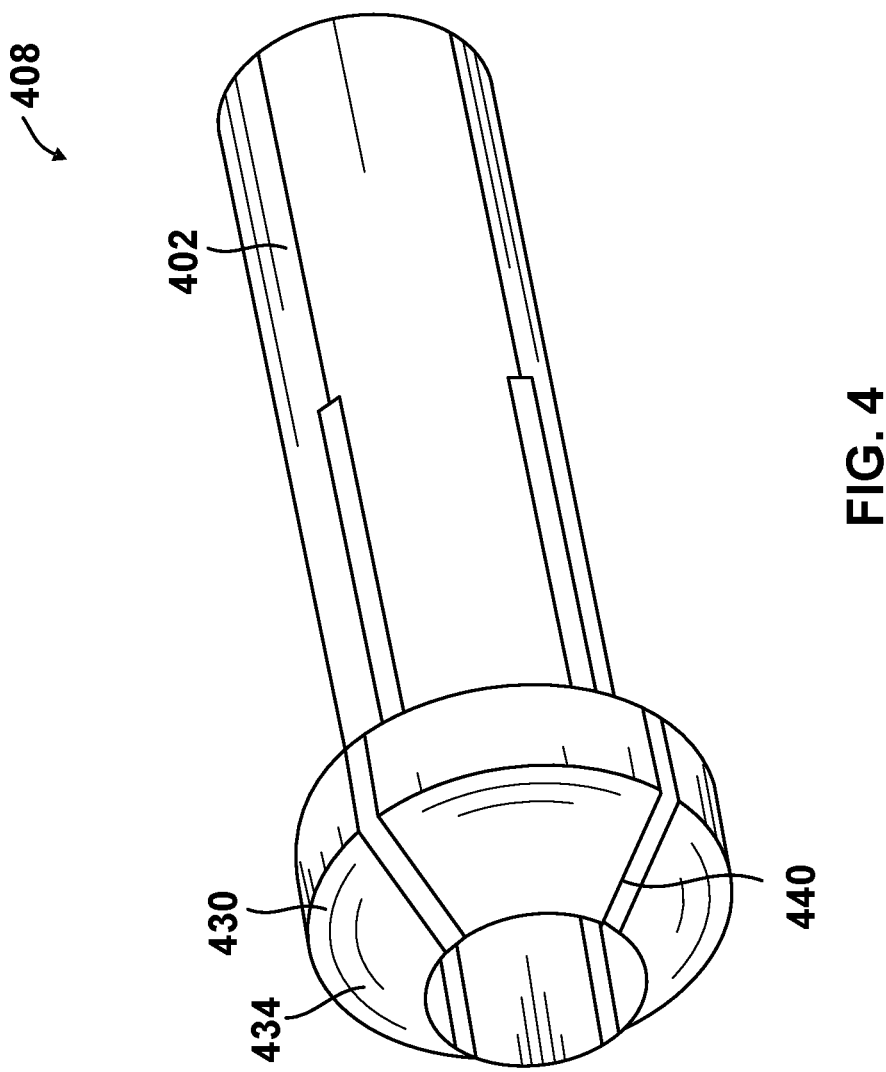
FIG. 4 is a perspective view of an example collet of a wire gripping device.
Figure 5:
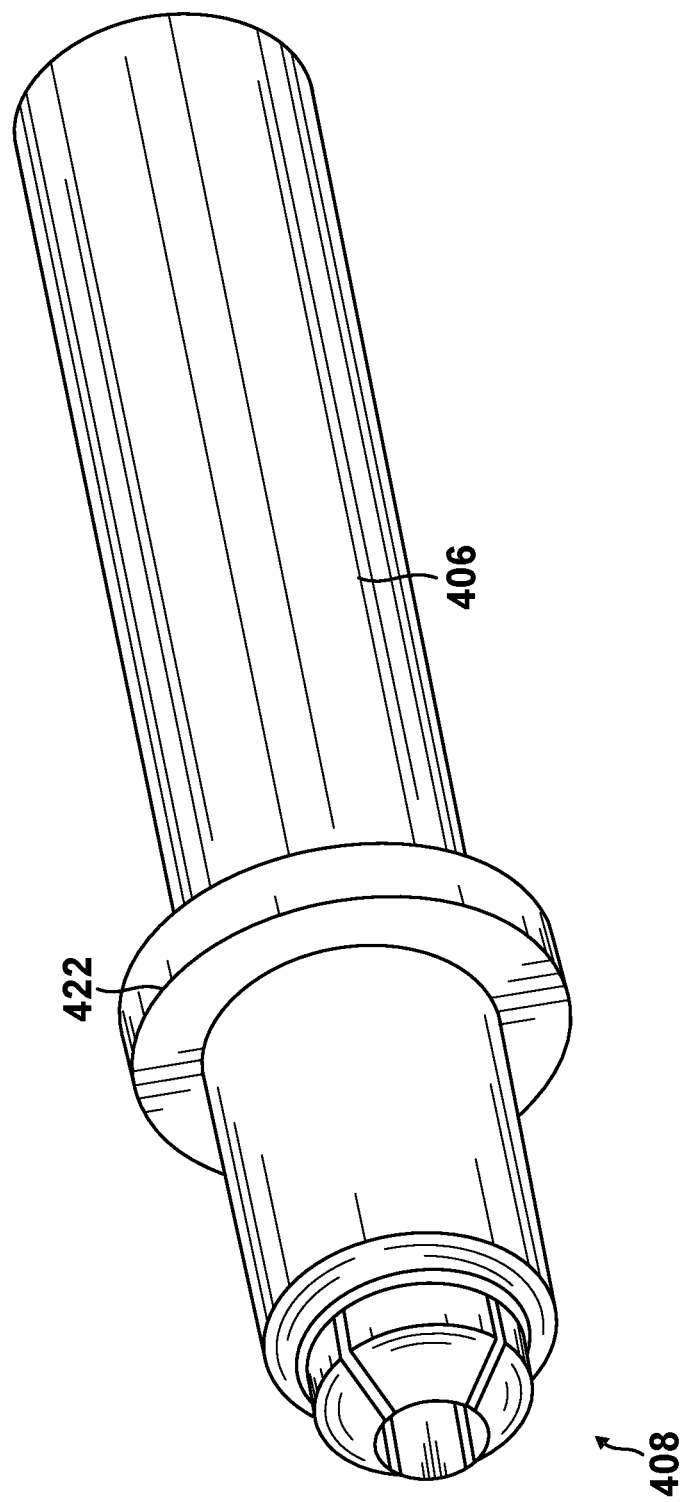
FIG. 5 is a perspective view of an example collet in a sleeve of a wire gripping device.
Figure 6:
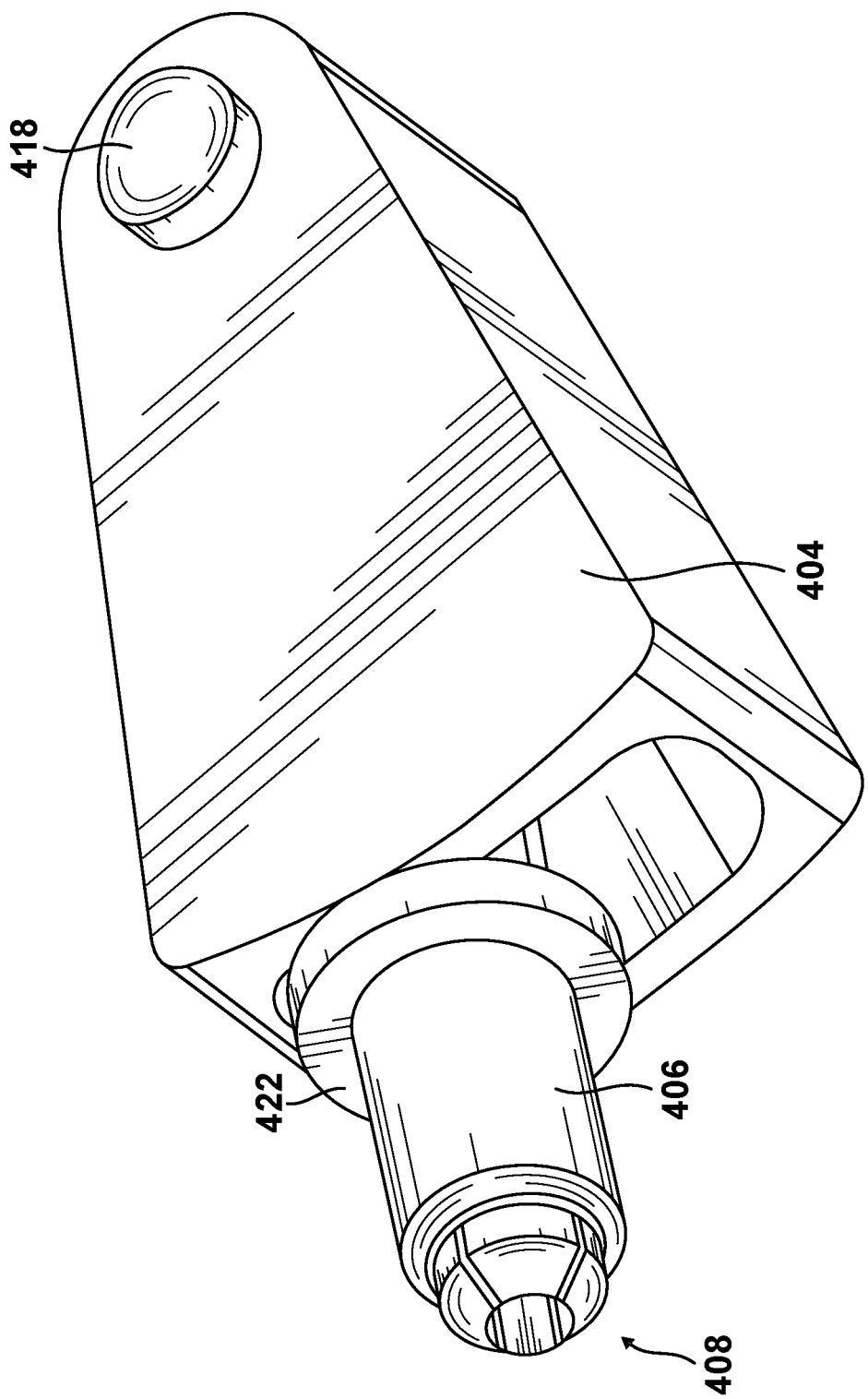
FIG. 6 is a perspective view of an example cam housing a collet in a collet sleeve of a wire gripping device.
Figure 7:
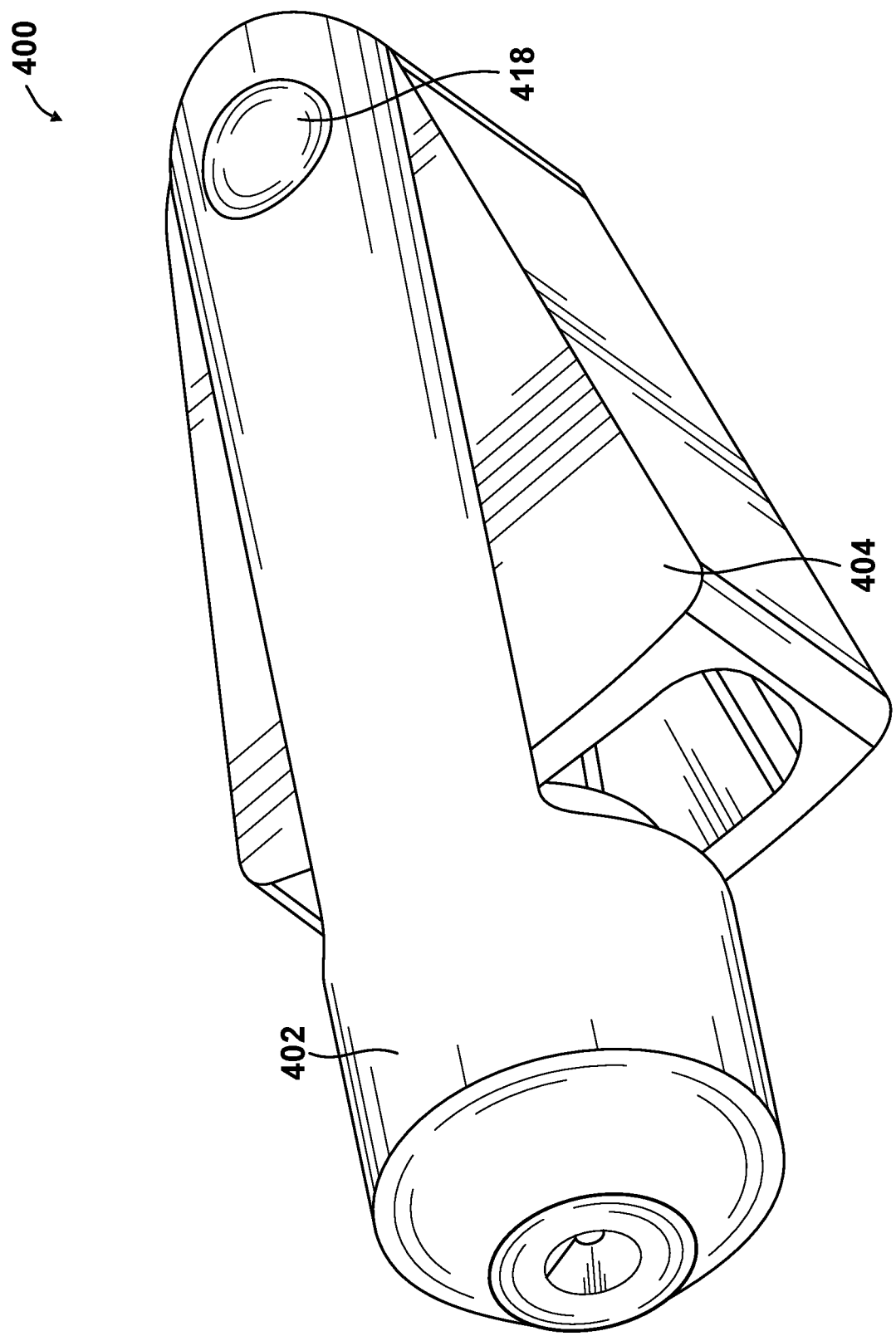
FIG. 7 is a perspective view of an example housing connected to a cam housing a collet in a collet sleeve of a wire gripping device.

FIGS. 4-7 illustrate example components of a wire gripping device 400 and how they fit together as a progression of adding wire gripping device 400 components starting from collet 408 illustrated in FIG. 4 to the entire wire gripping device 400 illustrated in FIG. 7.

FIG. 4 is a perspective view of an example collet 408, which is an example of collet 108. Collet 408 includes collet body 402, one or more tabs 430, and one or more slots 440. In the example shown, collet 408 may define a lumen configured to receive a medical device wire. Tabs 430 include proximal surfaces 434 that taper towards the proximal end of collet 408 and may be configured to engage with inner surfaces of a housing. Slots 440 are configured to allow collet 408 to compress in response to the application of a radially inwards force to tabs 430.

FIG. 5 is a perspective view of an example collet 408 partially housed within a collet sleeve 406, which is an example of collet sleeve 106. In the example shown, collet sleeve 406 includes flange 422. FIG. 6 is a perspective view of an example collet 408 partially housed within a collet sleeve 406 partially housed within a cam 404, which is an example of cam 104. In the example shown, cam 404 is near the release position relative to collet sleeve 406. FIG. 7 is a perspective view of an example housing 402 connected to cam 404. Housing 402 is an example of housing 102.

Figure 8:
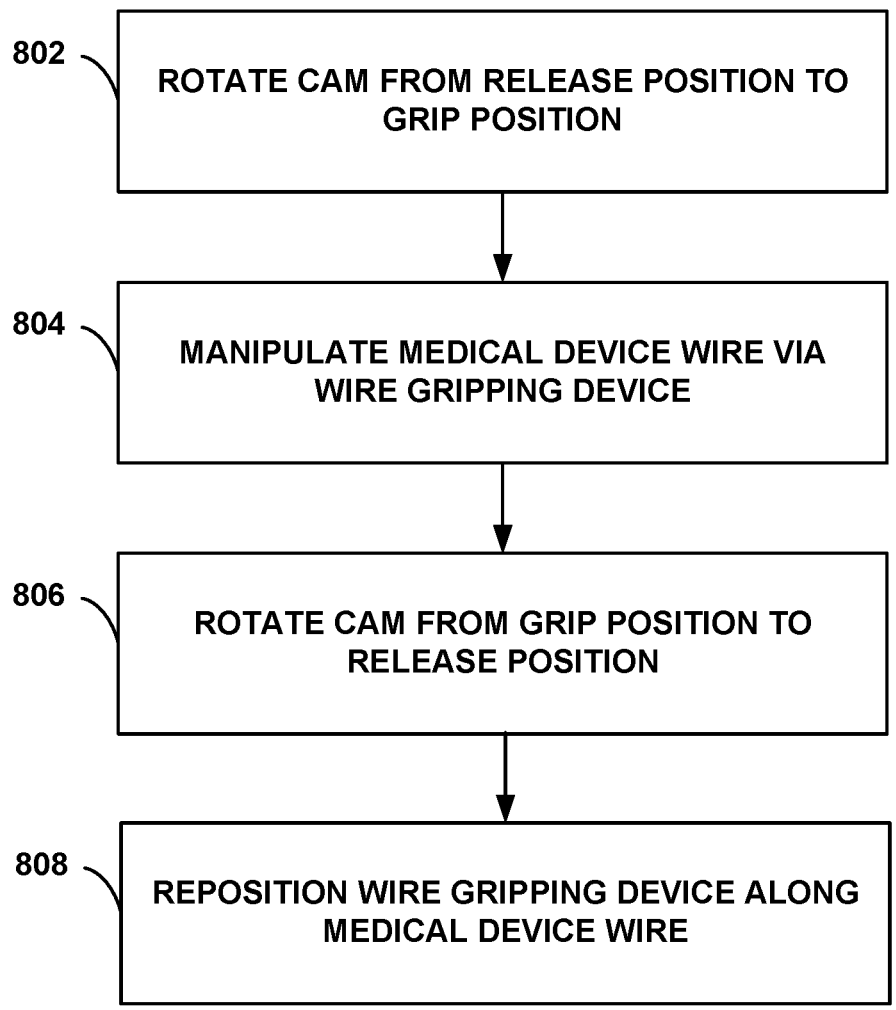
FIG. 8 is a flow diagram of an example method of using a wire gripping device.

FIG. 8 is a flow diagram of an example method of using a wire gripping device. While FIG. 8 is described with reference to wire gripping device 100, in other examples, the method can be used with other similar wire gripping devices, such as wire gripping device 400.

A user may introduce a medical device wire or shaft into a lumen of wire gripping device 100 (802). For example, a user may rotate cam 104 to the release position and slide wire gripping device 100 onto medical device wire 110 at one of the ends of medical device wire 110.

A user may rotate cam 104 from a release position to a grip position (804). For example, a user may push on cam 104 to rotate cam 104 relative to housing 102 in the grip direction C as illustrated in FIG. 1. In response to the rotation, cam 104 may push collet sleeve 106 towards proximal portion 112 of housing 102 via engaging with and/or contacting flange 122, and collet sleeve 106 may then push collet 108 towards proximal portion 112 of housing 102 in response to being pushed by cam 104. In some examples, cam 104 may push collet sleeve 106 in the proximal axial direction via pushing against apertures 116 of housing 102 in the distal axial direction via posts 118 mechanically connected to cam 104 and rotatably housed within apertures 116.

In response to being pushed, collet 108 may move in the proximal axial direction and proximal surfaces 134 of tabs 130 may engage with inner surfaces 132, which may cause a radially inwards force on tabs 130 proportional to an amount of the pushing of the collet sleeve. In response, collet 108 may compress, via slots 140, a lumen defined by collet 108 and configured to receive medical device wire 110, and thereby increase a grip force of collet 108 on medical device wire 110.

In some examples, a user may lock cam 104 in the grip position via rotating cam 104 all the way to the grip position. In some examples, a user may unlock cam 104 by applying a force to cam 104 in the release direction that is greater than a predetermined threshold force.

The user may manipulate medical device wire or shaft 110 via wire gripping device 100 and/or 400 (806). Once in the grip position, wire gripping device 100 may provide the user with a sufficient grip between wire gripping device 100 and medical device wire 110, and between wire gripping device 100 and a hand of the user. In some examples, the user may manipulate medical device wire 110 by torqueing (e.g., rotating about a central longitudinal axis) medical device wire 110 and/or pushing and pulling medical device wire 110. In some examples, the user may manipulate medical device wire 110 with wire gripping device 100 in the locked position, or in an unlocked position and gripping medical device wire 110 with a portion of the maximum grip force of wire gripping device 100, 400.

The user may rotate cam 104 from a grip position to a release position (808). For example, the user may push on cam 104 to rotate cam 104 relative to housing 102 in the release direction, e.g., a direction opposite direction C as illustrated in FIG. 1. In response to the rotation, cam 104 may reduce a push force on collet sleeve 106 towards proximal portion 112 of housing 102 via flange 122, and collet sleeve 106 may then reduce a push force against collet 108 towards proximal portion 112 of housing 102 in response to the reduced push force of cam 104. Collet 108 may then decompress via its radially outwards bias, e.g., its elastic force and/or spring force, and decrease a grip force on medical device wire 110. In response to the decompression of collet 108, tabs 130 may exert a radially outwards force on proximal surfaces 134, which may engage with inner surfaces 132 of housing 102 and cause collet 108 to move in the distal axial direction. Collet 108 may then push against and/or move collet sleeve 106 in the distal axial direction.

In some examples, the user may reposition wire gripping device 100 along medical device wire 110 (810). For example, the user may rotate cam 104 towards the release position, and/or to the release position, allowing collet 108 to decompress and reduce its grip on medical device wire, and/or release from medical device wire 110, thereby allowing wire gripping device 100 to move and/or slide along medical device wire 110. In some examples, the user may rotate cam 104 and reposition wire gripping device 100 with the same hand and/or a single hand. In some examples, the user may grip medical device wire 110, e.g., via rotating cam 104 towards the grip position, manipulate medical device wire 110, release medical device wire 110, e.g., via rotating cam 104 towards the release position, and reposition wire gripping device 100 all with a single hand.

Various examples of the disclosure have been described. Any combination of the described systems, operations, or functions is contemplated. These and other examples are within the scope of the following claims.

What is claimed is:

1. A device comprising:
    a collet defining a collet lumen, the collet lumen configured to receive a medical device wire or shaft;
    a collet sleeve configured to at least partially house the collet, wherein the collet sleeve defines a collet sleeve lumen configured to receive the medical device wire or shaft, wherein the collet sleeve comprises a flange; and
    a cam configured to at least partially house the collet sleeve, wherein the cam defines a cam lumen configured to receive the medical device wire or shaft; and
    a housing comprising:
        a proximal portion configured to at least partially house the collet and collet sleeve; and
        a distal portion, wherein the cam is rotatably attached to the distal portion,
    wherein the cam is configured to move the collet sleeve and collet towards the proximal portion of the housing upon rotation of the cam relative to the housing from a release position to a grip position,
    wherein the cam is configured to enable the collet sleeve and collet to move towards the distal portion of the housing upon rotation of the cam relative to the housing from the grip position to the release position.

2. The device of claim 1, wherein the medical device wire or shaft comprises a guidewire, a guide extension catheter wire, a wire coupled to an implant, or a tube or hypotube.

3. The device of claim 1, wherein a proximal end of the collet defines one or more slots, wherein the one or more slots are configured to compress radially inwards in response to rotation of the cam relative to the housing from the release position to the grip position.

4. The device of claim 1, wherein the collet comprises one or more tabs extending radially outwards at a proximal end of the collet, wherein a proximal surface of each tab tapers towards the proximal end of the collet.

5. The device of claim 4, wherein an inner surface of the proximal portion of the housing tapers towards a proximal end of the housing and is configured to engage the proximal surfaces of the one or more tabs.

6. The device of claim 5, wherein the collet sleeve is configured to move the collet towards the proximal portion of the housing upon being pushed by the cam, thereby forcing the proximal surfaces of the one or more tabs to engage the inner surface of the proximal portion of the housing, wherein the inner surface of the proximal portion of the housing is configured to resist movement of the collet and cause the one or more tabs to apply a radially inward force to compress the collet.

7. The device of claim 5, wherein the collet is biased radially outwards to enable the proximal surfaces of the one or more tabs to engage the inner surface of the proximal portion of housing and move the collet and collet sleeve in a distal direction relative to the housing upon rotation of the cam from the grip position to the release position.

8. The device of claim 7, wherein upon rotation of the cam from the grip position to the release position, a diameter of the collet lumen is configured to increase and thereby decrease a grip force on the medical device wire or shaft.

9. The device of claim 1, wherein rotation of the cam from the release position to the grip position is configured to compress the collet, and wherein the collet is configured to decrease a diameter of the collet lumen and increase a grip force on the medical device wire or shaft upon compression of the collet.

10. The device of claim 1, wherein the cam comprises one or more posts, the one or more posts configured to be rotatably attached within one or more apertures of the housing, wherein the cam is configured to push the housing in a distal direction via the one or more posts while pushing the collet sleeve in a proximal direction via the flange.

11. The device of claim 4, wherein the cam is configured to apply a radial force compressing the collet, via the one or more tabs, in response to rotation of the cam relative to the housing.

12. The device of claim 1, wherein the cam is configured to remain in the grip position until a force greater than a predetermined threshold force is applied to the cam in a release direction.

13. A method comprising:
introducing a medical device wire or shaft into a device lumen of a device, wherein the device comprises:
a collet defining a collet lumen;
a collet sleeve configured to at least partially house the collet, wherein the collet sleeve defines a collet sleeve lumen, wherein the collet sleeve comprises a flange; and
a cam configured to at least partially house the collet sleeve, wherein the cam defines a cam lumen; and
a housing comprising:
a proximal portion configured to at least partially house the collet and collet sleeve; and
a distal portion, wherein the cam is rotatably attached to the distal portion,
wherein the device lumen is at least partially defined by the collet lumen, the collet sleeve lumen, and the cam lumen;
rotating the cam relative to the housing from a release position towards a grip position,
wherein the cam is configured to move the collet sleeve and collet towards the proximal portion of the housing upon rotation of the cam relative to the housing from the release position to the grip position, and
wherein the cam is configured to enable the collet sleeve and collet to move towards the distal portion of the housing upon rotation of the cam relative to the housing from the grip position to the release position.

14. The method of claim 13, wherein the medical device wire or shaft comprises a guidewire, a guide extension catheter wire, a wire coupled to an implant, or a tube or hypotube.

15. The method of claim 13, wherein a proximal end of the collet defines one or more slots, wherein rotating the cam from the release position towards the grip position comprises compressing the one or more slots radially inwards.

16. The method of claim 13, further comprising:
rotating the cam from the grip position towards the release position; and
repositioning the device along the medical device wire or shaft.

17. The method of claim 13, further comprising:
locking the cam in the grip position until a force greater than a predetermined threshold force is applied to the cam in a release direction.

18. A medical device comprising:
a collet defining a collet lumen, the collet lumen configured to receive a medical device wire or shaft;
a collet sleeve configured to at least partially house the collet, wherein the collet sleeve defines a sleeve lumen configured to receive the medical device wire or shaft, wherein the collet sleeve comprises a flange; and
a cam configured to at least partially house the collet sleeve, wherein the cam defines a cam lumen configured to receive the medical device wire or shaft; and
a housing comprising:
a proximal portion configured to at least partially house the collet and collet sleeve; and
a distal portion, wherein the cam is rotatably attached to the distal portion,
wherein the cam is configured to increase a push force against the flange upon rotation of the cam relative to the housing from a release position to a grip position and thereby move the collet sleeve and collet towards the proximal portion of the housing,
wherein the cam is configured to move the collet sleeve and collet towards the proximal portion of the housing upon rotation of the cam relative to the housing from a release position to a grip position,
wherein the cam is configured to enable the collet sleeve and collet to move towards the distal portion of the housing upon rotation of the cam relative to the housing from the grip position to the release position,
wherein rotation of the cam from the release position to the grip position is configured to compress the collet, and wherein the collet is configured to decrease a diameter of the collet lumen and increase a grip force on the medical device wire or shaft upon compression of the collet.

19. The medical device of claim 18, wherein upon rotation of the cam from the grip position to the release position, the diameter of the collet lumen is configured to increase to decrease the grip force on the medical device.

20. The medical device of claim 18, wherein the cam is configured to remain in the grip position until a force greater than a predetermined threshold force is applied to the cam in a release direction.

21. The device of claim 1, wherein the cam comprises a post positioned at a distal portion of the cam, wherein the cam is rotatably attached to the distal portion of the housing by the post, wherein the cam is configured to rotate about the post relative to the housing, wherein the cam is configured to move the collet sleeve by pushing on the housing via the post.

22. The device of claim 21, wherein a length of the cam between the post and the flange when the cam is in the grip position is greater than the length of the cam between the post and the flange when the cam is in the release position.

23. The device of claim 1, wherein the cam comprises a tapered inner surface configured to mate with the collet sleeve and lock the cam in at least one of the grip position or the release position until a force greater than a predetermined threshold force is applied to the cam.

* * * * *